(12) United States Patent
Olsen

(10) Patent No.: US 7,908,900 B2
(45) Date of Patent: Mar. 22, 2011

(54) FRICTION MEASURING DEVICE

(76) Inventor: Thor Wiggo Olsen, Oslo (NO)

(*) Notice: Subject to any disclaimer, the term of this patent is extended or adjusted under 35 U.S.C. 154(b) by 333 days.

(21) Appl. No.: 11/992,484

(22) PCT Filed: Oct. 5, 2006

(86) PCT No.: PCT/NO2006/000342
§ 371 (c)(1),
(2), (4) Date: Jun. 16, 2008

(87) PCT Pub. No.: WO2007/040409
PCT Pub. Date: Apr. 12, 2007

(65) Prior Publication Data
US 2010/0192665 A1 Aug. 5, 2010

(30) Foreign Application Priority Data
Oct. 6, 2005 (NO) .................................. 20054591

(51) Int. Cl.
*G01N 19/02* (2006.01)
(52) U.S. Cl. .............................................................. 73/9
(58) Field of Classification Search .................... 73/9
See application file for complete search history.

(56) References Cited

U.S. PATENT DOCUMENTS

| | | | | |
|---|---|---|---|---|
| 3,367,170 A * | 2/1968 | Lynch et al. | .......................... | 73/9 |
| 3,538,742 A * | 11/1970 | Benning | .............................. | 73/9 |
| 4,050,290 A * | 9/1977 | Lonnroth | .............................. | 73/9 |
| 4,098,111 A * | 7/1978 | Hardmark et al. | ................... | 73/9 |
| 4,130,008 A * | 12/1978 | Broshears | ............................ | 73/9 |
| 4,134,291 A * | 1/1979 | Gregoire | .......................... | 73/862 |
| 4,144,748 A * | 3/1979 | Vinogradov et al. | ............ | 73/146 |
| 4,594,878 A * | 6/1986 | Abe et al. | ............................ | 73/9 |
| 4,662,211 A * | 5/1987 | Strong | .................................. | 73/9 |
| 4,779,447 A * | 10/1988 | Rath | ...................................... | 73/9 |
| 4,909,073 A | 3/1990 | Takahashi et al. | | |
| 4,955,933 A * | 9/1990 | Sistonen | ............................. | 73/9 |
| 5,814,718 A * | 9/1998 | Andresen et al. | ................... | 73/9 |
| 6,427,519 B2 * | 8/2002 | Ueda et al. | ........................... | 73/9 |
| 6,463,784 B2 * | 10/2002 | Kashiwagi et al. | ................. | 73/9 |
| 6,681,614 B1 | 1/2004 | Riffe | | |

(Continued)

FOREIGN PATENT DOCUMENTS

DE    27 42 110    3/1979

(Continued)

OTHER PUBLICATIONS

Official English-language translation of JP 1995006856 B2, originally published on Jan. 30, 1995.*

(Continued)

*Primary Examiner* — David A. Rogers
(74) *Attorney, Agent, or Firm* — Wenderoth, Lind & Ponack, L.L.P.

(57) ABSTRACT

A device and method for measuring friction on a surface, such as a road, allow for accurate and reliable measurements by preventing the slipping of a pilot wheel. The device includes a pilot wheel and a measurement wheel mounted on shafts in a wheel box and arranged one behind the other, the pilot wheel rotating without slip and the measurement wheel being braked in order to provide slip. The configuration of the device, including the positioning of an attachment axle, results in the pilot wheel being subjected to greater ground pressure than the measurement wheel, thus preventing slipping of the pilot wheel.

13 Claims, 4 Drawing Sheets

U.S. PATENT DOCUMENTS

| | | | |
|---|---|---|---|
| 6,923,038 B2 * | 8/2005 | Klovning | 73/9 |
| 7,117,716 B2 * | 10/2006 | Neubert et al. | 73/9 |
| 7,509,847 B2 * | 3/2009 | Halliday | 73/146 |
| 2004/0144167 A1 | 7/2004 | Halliday | |

FOREIGN PATENT DOCUMENTS

| | | | |
|---|---|---|---|
| DE | 28 23 486 | | 12/1979 |
| DE | 3438225 | A1 * | 5/1986 |
| GB | 1 269 334 | | 4/1972 |
| JP | 04102034 | A * | 4/1992 |
| JP | 11326539 | A * | 11/1999 |
| JP | 2004017917 | A * | 1/2004 |
| SU | 1087839 | | 4/1984 |
| SU | 1823834 | A3 * | 6/1993 |

OTHER PUBLICATIONS

International Search Report mailed Jan. 17, 2007 for International Application No. PCT/NO06/000342.

International Preliminary Report on Patentability mailed Jan. 25, 2008 for International Application No. PCT/NO06/000342.

* cited by examiner

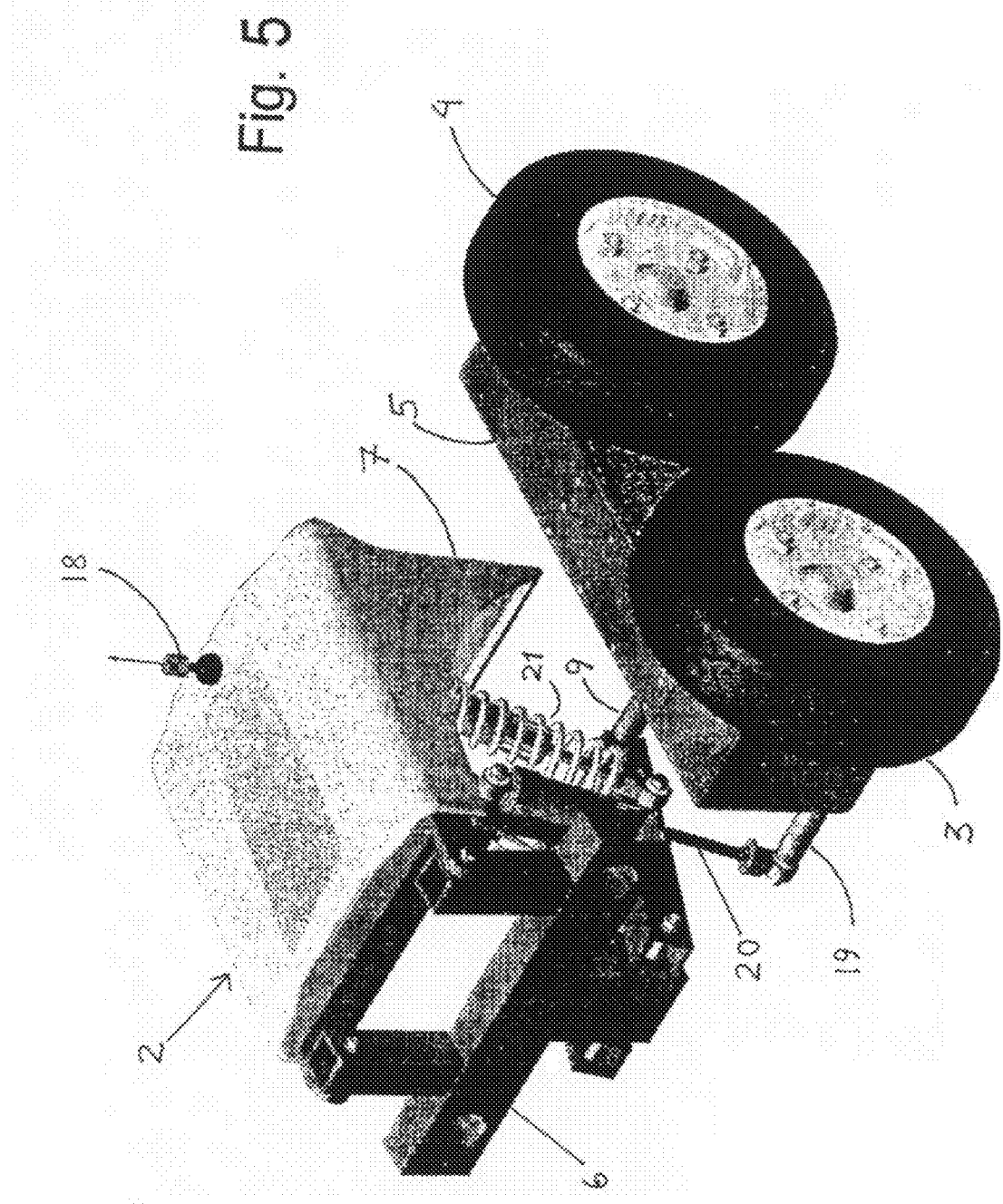

FRICTION MEASURING DEVICE

BACKGROUND OF THE INVENTION (1) Field of the Invention

The present invention relates to measuring friction on a physical surface, preferably a roadway, where a measuring device on wheels is pulled by a traction vehicle. One of the wheels of the measuring device is braked during driving, so that this wheel provides slip against the surface.

For the office in charge of roads (in Norway, the Public Roads Administration or the municipalities), there is a requirement that roads must exhibit a friction minimum value between the roadway and a car wheel. This is particularly important in winter. A standardized method of measuring has been established, namely with a fixed slip value and with measurement in a wheel track. This is to be documented, with respect to contracts, by the office in charge of roads as well as the contractor.

Friction measurement is simple in theory, but difficult to execute in practice. Measuring devices available today are complicated and expensive, and in most cases they are adapted to airports, with a measuring wheel mounted between the wheel tracks of the traction vehicle. This is a set-up poorly adapted for use in a road, since the traction vehicle/the car must drive outside the usual tracks in order to place the measuring wheel in a wheel track. In other words, there is a need of a measuring device better adapted to the situation in a normal road.

(2) Description of the Related Art

A measurement principle relied on by several previously known measuring devices has two wheels connected to each other by means of a chain or similar, where one wheel is a "pilot wheel" rotating with a periphery speed equal to the driving speed, that is without slip, and where the other wheel is braked to a slip value (which means that this other wheel skids on the roadway and has a lower periphery speed than the driving speed). Since the two wheels are connected to each other, a "break" will arise between the two wheels, which "break" can be measured in the chain (or another force/moment transfer means) by means of a load cell.

Related art is known from British patent number 1,269,334, DE "Offenlegungsschrift" 2742110 and U.S. Pat. No. 4,909,073, all disclosing devices for measuring friction on a road surface, using two wheels. The wheels are arranged in a frame, a box or a housing, and they are typically arranged on one and the same shaft. The wheels rotate with different rotation speeds against the underlying road surface.

Because the two wheels are arranged beside each other on one and the same shaft, they are actually not capable of measuring friction precisely in one wheel track. And in the closest one of these publications, namely U.S. Pat. No. 4,909,073, which uses a measurement principle that lies rather close to the one used in the present invention, with measurement of load in a force/moment transfer means between two connected wheels with a "transmission ratio", no device has been disclosed to ensure that one of the two wheels, namely the "pilot wheel" intended to roll without slip, will actually be unable to have slip. With the solution in U.S. Pat. No. 4,909,073, it seems clear that in certain situations, one may have a "return" reaction moment to the pilot wheel, resulting in a slip situation for this wheel also. A rather unfavourable instability will then be induced in the measurements.

Further, Japanese publication JP 4,102,034 discloses a friction measurement device in which two wheels are mounted behind each other in a frame, for measurement in one wheel track.

BRIEF SUMMARY OF THE INVENTION

The present invention has the aim to provide a solution that will have a reasonable price and a simple construction, makes a genuine measurement in one wheel track, and is safeguarded, by way of its construction, against measurement instabilities by preventing a slip condition for the pilot wheel.

Hence, in accordance with the present invention there is provided a method for measuring friction such as defined precisely in the appended claims, and a friction measuring device such as defined precisely in the appended claims. Favourable embodiments of the friction measuring device in accordance with the invention are also set forth in the claims.

As a result of the feature that the two wheels in the measuring device are arranged right behind each other, a possibility is secured for a genuine measurement in one roadway wheel track, and by attaching the chain cover to the main unit using an attachment axle positioned markedly closer to one wheel than the other, this closest wheel will achieve an increase in ground pressure relative to the other wheel, the other wheel being the braked wheel. Hence, stable measurements are ensured, and variations induced by a sudden slip for the pilot wheel are avoided.

Further assurance of stability in the measurements can be achieved by mounting the force sensor near the measurement wheel. Vibrations in the force/moment transfer means close to the force sensor are then avoided.

BRIEF DESCRIPTION OF THE DRAWINGS

The invention shall now be described in more detail by going through embodiments thereof, and in this connection it is also referred to the appended drawings, of which FIG. 5 shows a concrete embodiment example of a friction measuring device in accordance with the invention.

DETAILED DESCRIPTION OF THE INVENTION

Figure 1:
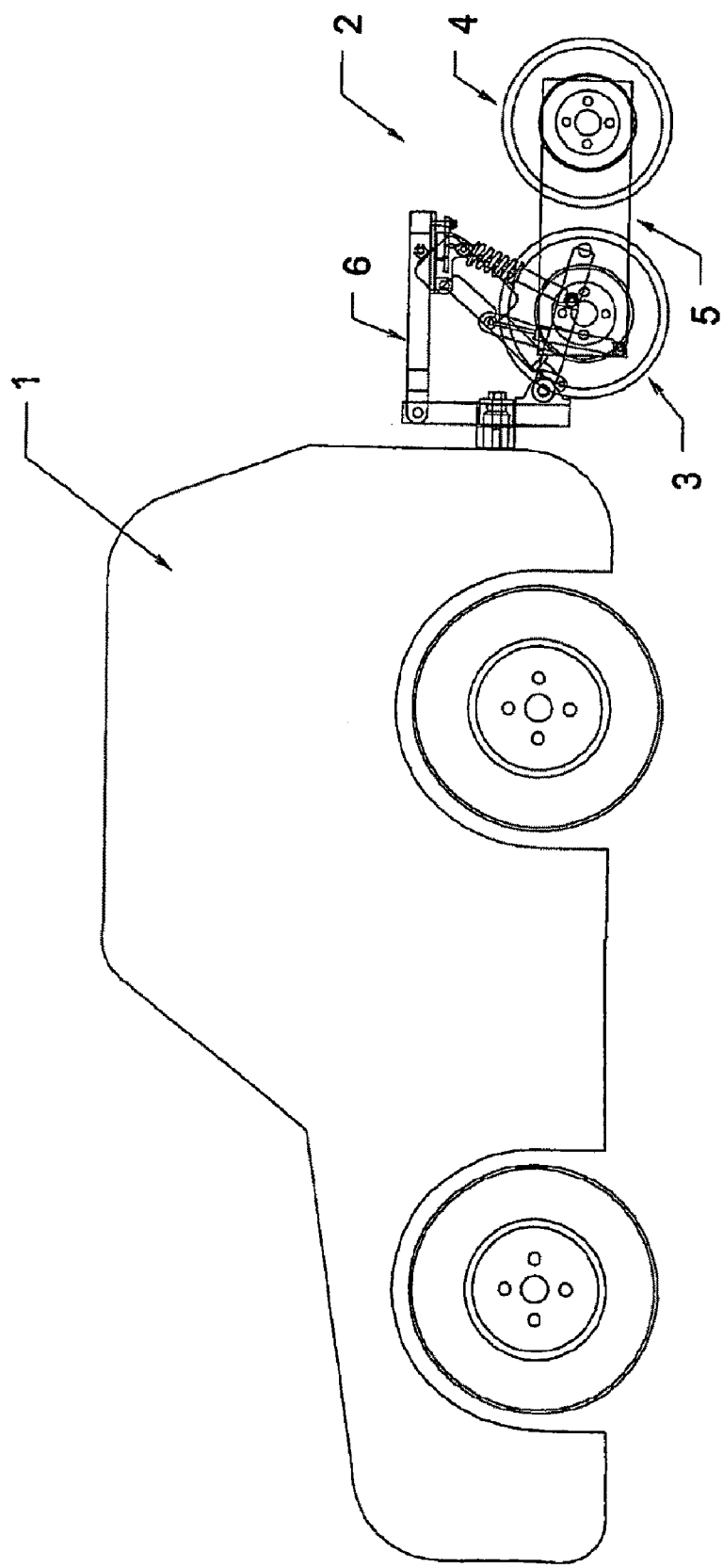
FIG. 1 shows an exemplary embodiment of a friction measuring device in accordance with the invention, mounted behind a traction vehicle.

FIG. 1 shows a traction vehicle 1, in this case an ordinary car, pulling a friction measuring device 2 on a surface that has not been drawn. The surface is normally a road surface. Important elements in the friction measuring device 2 as shown, are a forward wheel 3, a rear wheel 4, a common wheel box or chain cover 5, as well as a main unit 6 to which the chain cover 5 is attached, and which in its turn is attached to the rear end of vehicle 1.

Figure 2:
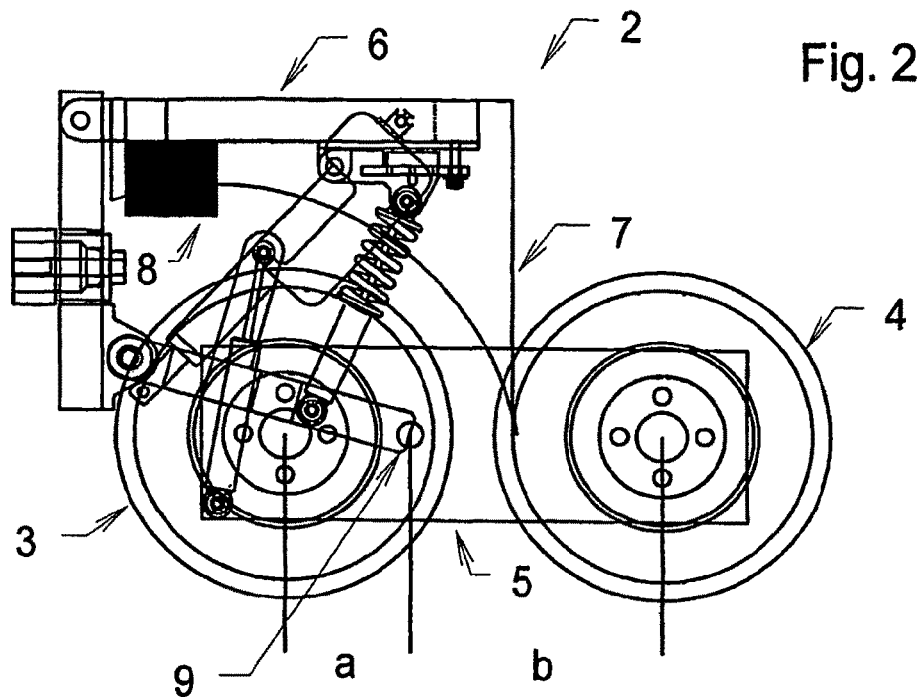
FIG. 2 shows substantially the same embodiment of the friction measuring device as in FIG. 1, however in closer detail.

In FIG. 2 appears a somewhat different embodiment of the friction measuring device 2, than the embodiment shown in FIG. 1, however the most important elements are the same. Main unit 6 is shaped more like a box, having a housing 7 that extends somewhat downwards, and inside housing 7 there is a data processing box 8. An important element is an attachment axle 9 that attaches chain cover 5 to the main unit 6. The location of this attachment axle 9 appears clearly as being substantially closer to the axis of one wheel (in this case forward wheel 3) than to the axis of the other wheel, see distance indications a and b.

The gist of this "eccentric" placing of the main unit attachment point on the chain 5 cover, is to ensure that one wheel, in this embodiment forward wheel 3, is guaranteed to have a heavier ground pressure than the other wheel.

Concurrently with this placing of the attachment point 9, the wheels are arranged in such a manner that the forward wheel 3 shall be a pilot wheel intended to rotate without slip, while the rear wheel 4 shall be kept in a slip condition during operation.

Figure 3:
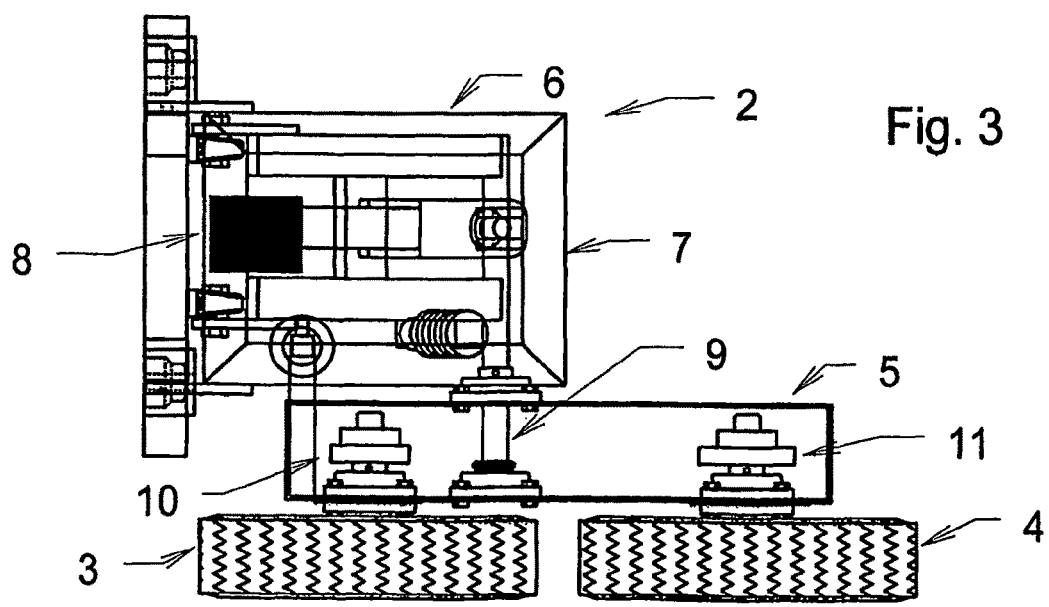
FIG. 3 shows the same device as FIG. 2, however in a top view.

The manner of achieving a slip condition for the rear wheel 4, appears partly from FIG. 3 that shows the same friction measuring device 2 as FIG. 2, but in a top view. It appears inside the chain cover 5 that the two wheels are provided with differently sized sprocket wheels on their respective shafts, for instance the forward sprocket wheel 10 may have 20 teeth, while sprocket wheel 11 at the rear wheel 4 may have 24 teeth. It is of course possible to use other sizes of the sprocket wheels in order to provide other transmission ratios.

At the same time it should be noted that the force/moment transfer means between the two wheels is not necessarily a chain device, for instance a cardan means may be used instead.

Figure 4:
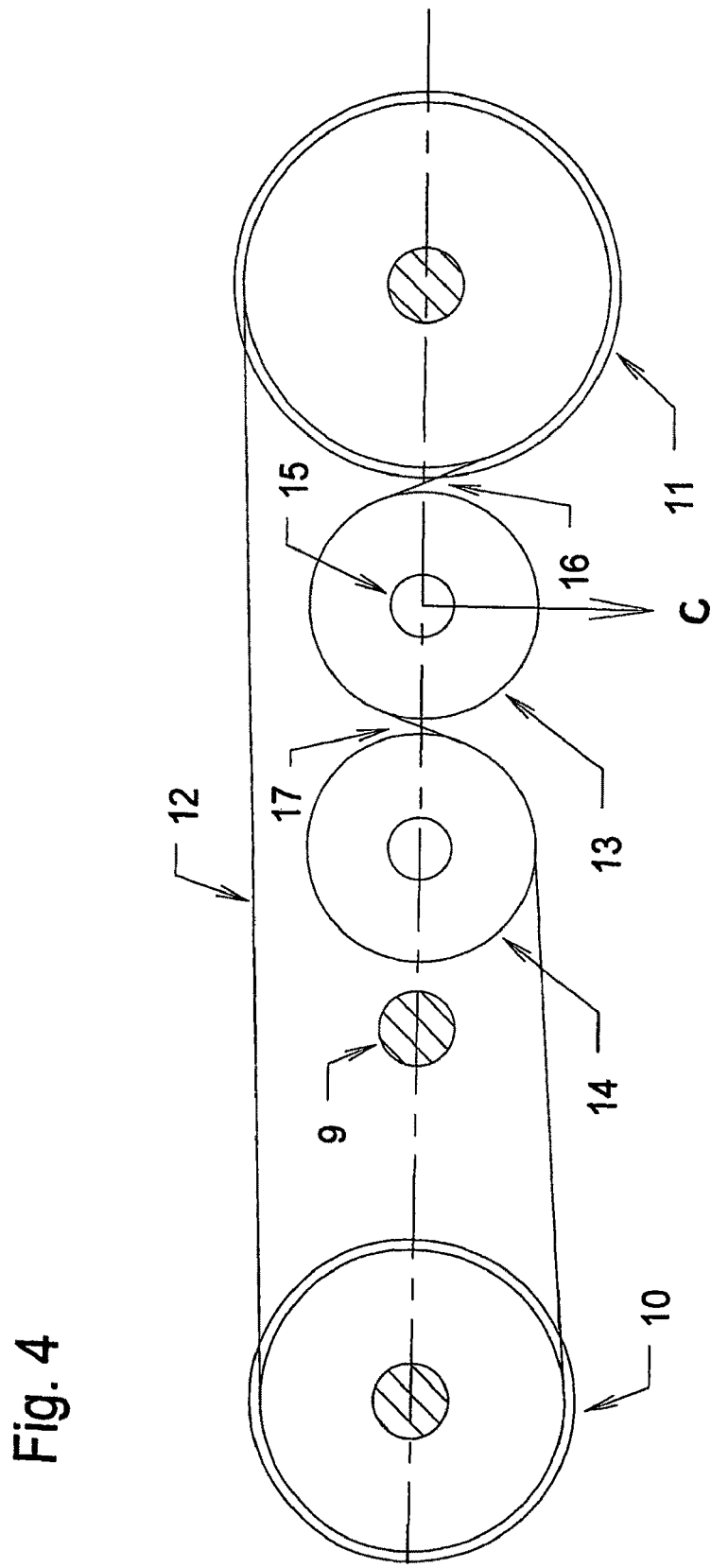
FIG. 4 is a principle sketch showing an embodiment of a force/moment transfer means that is part of the friction measuring device.

In FIG. 3, the chain encircles sprocket wheels 10 and 11 is not shown, but it is referred instead to FIG. 4, which drawing shows a simplified sketch of the chain drive principle in the friction measuring device disclosed in FIGS. 2 and 3. It is referred to sprocket wheels 10 and 11, of which ref 10 is attached to forward wheel 3 that in this embodiment is a pilot wheel intended to roll without slip. Sprocket wheel 10 is smaller than sprocket wheel 11 which will then rotate somewhat slower, and thereby the rear wheel 4 is braked to have a slip situation. In FIG. 4 appears also attachment point 9, to ensure that the ground pressure is largest for forward wheel 3: The chain is indicated by reference numeral 12, and two additional sprocket wheels 13 and 14 are inserted to provide a possibility for measuring stress in chain 12. At the center of sprocket wheel 13 there is a load cell 15 able to measure vertical load c, and this vertical load is directly related to the tension in chain 12. Sprocket wheel 13 is arranged rather close to the large sprocket wheel 11, and furthermore, sprocket wheel 14 is arranged rather close to sprocket wheel 13. This means that the free lengths or runs of chain 12 between sprocket wheel 14 and the large sprocket wheel are short. These lengths are indicated by reference numerals 16 and 17. The points of having lengths 16 and 17 short, is that the chain will then have a very small tendency to vibrate or swing, and consequently further stability is achieved for the load cell measurement.

In the shown embodiment, pilot wheel 3 is the forward wheel, while measurement wheel 4 is the rear wheel. This might equally well be reversed, but in such a case, the attachment axle 9 must be located closer to the rear wheel instead.

In FIG. 5 appears a practical embodiment of the friction measuring device in accordance with the invention. In addition to the already mentioned details like wheels 3 and 4, wheel box/chain cover 5, main unit 6, housing 7 and attachment axle 9, there appears an antenna 18 for short distance transmission of data to a PC/display equipment that may preferably be located inside the traction vehicle. Furthermore, the friction measuring device 2 is equipped with a suspension system, in which a combined spring/shock absorber 21 constitutes the main cushioning for chain cover 5 and wheels 3, 4, while an additional shock absorber 20 is mounted to a front stay 19 on the chain cover in order to counteract vibrations and shocks that would otherwise cause pivoting about the attachment axle 9.

A measurement signal from load cell 15 (FIG. 4) is transmitted, on a not shown wire, to data processing box 8 (FIGS. 2, 3) in which calculations and recordings are executed. The data box may also, as appears from the above, transmit signals via antenna 18, or via wiring, to further equipment carried in the traction car.

It is possible to make compensations on a continuous basis in the friction result, for changes in the ground pressure during the measuring operation. The ground pressure is measured continuously by a (not shown) load cell at the top of shock absorber/spring 21. This shock absorber is pushed down by a load from the car, and weighs down the wheels of the measuring device against the roadway with an adjusted ground pressure for the measurement wheel. When the ground pressure is changed due to irregularities in the road surface and car springing action caused thereby, these changes are compensated for by computer, in order to obtain stable friction measurements.

In an alternative embodiment (not shown in any drawing), the main unit may be mounted to a frame arranged underneath the traction vehicle, which may possibly be a large vehicle (truck). The frame may then be arranged between the wheel sets of the vehicle, i.e. in front of a rear wheel set, or between front and rear wheels. In any case, the sideways location must be such that the two wheels of the friction measuring device roll in line with a wheel track of the vehicle.

The most important features of the invention can be summarized as follows:

By having the two wheels 3, 4 of the friction measuring device mounted behind each other in the wheel track, measurements are made in the correct place, and by giving one of the wheels (the forward wheel) 3 the largest ground pressure, one ensures that this wheel will always have a periphery speed equal to the driving speed, which means that this wheel rolls without slip. The other wheel (the rear wheel) will always be the wheel that slips (skids), and this fact will guarantee a stable measurement result.

In order to achieve this in a simple manner, the two wheels are mounted, in accordance with the invention, to a common wheel box/chain cover 5 that has a common attachment axle 9 to the main unit 6. The attachment axle 9 is placed with an offset, that is closer to one wheel than the other wheel, in order to provide a larger ground pressure for said one wheel than for the other, which other wheel is a measurement wheel with slip.

In addition, it is favourable that the force sensor (load cell 15) is mounted as close to the measurement wheel 4 as possible, especially in a chain solution. Swinging in a chain will ordinarily influence the force sensor and add pulses, that is variations in the friction measurements, but with a location close to the measurement wheel, the chain influence on the load cell will be reduced significantly.

The friction measuring device in accordance with the invention is preferably mounted directly at the rear of the traction vehicle/car with two attachment points. One attachment may be an ordinary towing bracket, and the other one will be a coupling 5 point mounted at the corner of the car, or in a bumper bracket.

The invention claimed is:

1. A method for measuring friction on a road surface, the method comprising:

pulling a main unit along a measurement area, the main unit being supported by a pilot wheel and a measurement wheel, the pilot wheel rotating without slip and the measurement wheel being braked in order to provide slip, wherein the pilot wheel and the measurement wheel are arranged one behind the other and are mounted on shafts in a wheel box, the wheel box being disposed at a side of the main unit, and wherein the pilot wheel and the measurement wheel are rotationally connected by a force/moment transfer means; and measuring stress in the force/moment transfer means, wherein the main unit is connected to the wheel box by an attachment axle, the attachment axle being attached to the wheel box closer to the pilot wheel than the measurement wheel such that the pilot wheel is subjected to greater ground pressure than the measurement wheel.

2. The method of claim 1, wherein the main unit transmits a downward force to the attachment axle such that a larger force is exerted on the pilot wheel than the measurement wheel.

3. The method of claim 1, wherein the main unit transmits a downward force to the attachment axle, and the friction measuring device is configured such that the downward force is transmitted to the pilot wheel and the measurement wheel through the wheel box such that a larger force is exerted on the pilot wheel than the measurement wheel.

4. The method of claim 1, wherein the main unit includes a shock absorber which transmits a downward force to the attachment axle, and the friction measuring device is configured such that the downward force is transmitted to the pilot wheel and the measurement wheel through the wheel box such that a larger force is exerted on the pilot wheel than the measurement wheel.

5. A friction measuring device for measuring friction on a surface, the friction measuring device comprising:

a main unit;

a pilot wheel and a measurement wheel mounted on shafts in a wheel box and arranged one behind the other in a measurement direction, said pilot wheel rotating without slip and said measurement wheel being braked in order to provide slip;

a force/moment transfer means rotationally connecting said pilot wheel and said measurement wheel;

a force sensor arranged to measure stress in said force/moment transfer means; and processing and recording equipment;

wherein said main unit is mechanically and releasably connectable to a traction vehicle, and said wheel box in mounted at a side of said main unit by an attachment axle, wherein said attachment axle is attached to said wheel box closer to said pilot wheel than said measurement wheel such that said pilot wheel is subjected to greater ground pressure than said measurement wheel.

6. The friction measuring device of claim 5, wherein said force sensor is mounted adjacent to said measurement wheel in order to increase stability in the measurements.

7. The friction measuring device of claim 5, wherein said force/moment transfer means includes a chain and includes sprocket wheels of different sizes on said shafts of said pilot wheel and said measurement wheel, said chain being disposed around said sprocket wheels.

8. The friction measuring device of claim 5, wherein said main unit is mounted directly on the traction vehicle and arranged such that the two wheels follow the same track as one of the wheel tracks of the traction vehicle.

9. The friction measuring device of claim 5, wherein said main unit transmits a downward force to said attachment axle such that a larger force is exerted on said pilot wheel than said measurement wheel.

10. The friction measuring device of claim 5, wherein said main unit transmits a downward force to said attachment axle, and said friction measuring device is configured such that the downward force is transmitted to said pilot wheel and said measurement wheel through said wheel box such that a larger force is exerted on said pilot wheel than said measurement wheel.

11. The friction measuring device of claim 5, wherein said main unit includes a shock absorber which transmits a downward force to said attachment axle, and said friction measuring device is configured such that the downward force is transmitted to said pilot wheel and said measurement wheel through said wheel box such that a larger force is exerted on said pilot wheel than said measurement wheel.

12. The friction measuring device of claim 5, wherein said processing and recording equipment is arranged in said main unit.

13. The friction measuring device of claim 12, wherein the traction vehicle is a car and the surface is a road surface, and wherein data display and recording equipment is arranged inside the car for receiving data transmitted in real time from said processing and recording equipment in said main unit.

* * * * *